United States Patent [19]
Murase et al.

[11] Patent Number: 5,530,192
[45] Date of Patent: Jun. 25, 1996

[54] OILSEED CROPS PRODUCING VALUABLE SEEDS HAVING ALTERED AMINO ACID COMPOSITION AND FATTY ACID COMPOSITION

[75] Inventors: Junko Murase; Jun Imamura, both of Machida, Japan

[73] Assignees: Mitsubishi Corporation; Mitsubishi Kasei Corporation, both of Tokyo, Japan

[21] Appl. No.: 218,239

[22] Filed: Mar. 28, 1994

[30] Foreign Application Priority Data

Mar. 31, 1993 [JP] Japan .................................. 5-073806

[51] Int. Cl.$^6$ ............................. A01H 5/00; C07H 21/04; C12N 15/29; C12N 15/82
[52] U.S. Cl. .................................. 800/205; 800/DIG. 69; 800/DIG. 70; 536/24.5; 435/172.3; 435/320.1
[58] Field of Search .......................... 536/24.5; 800/205, 800/DIG. 69, DIG. 70; 435/172.3, 320.1

[56] References Cited

U.S. PATENT DOCUMENTS

| | | | |
|---|---|---|---|
| 5,107,065 | 4/1992 | Shewmaker et al. | 800/205 |
| 5,188,958 | 2/1993 | Moloney et al. | 435/240 |

FOREIGN PATENT DOCUMENTS

| | | |
|---|---|---|
| 0412006 | 2/1991 | European Pat. Off. . |
| 0515048A1 | 11/1992 | European Pat. Off. . |
| 0591530A1 | 4/1994 | European Pat. Off. . |
| 90/10380 | 9/1990 | WIPO . |
| 91/15578 | 10/1991 | WIPO . |
| 93/18643 | 9/1993 | WIPO . |

OTHER PUBLICATIONS

Fujiwara et al., "Seed–specific repression of GUS activity in tobacco plants by antisense RNA", Plant Molecular Biology 20: pp. 1059–1069, 1992.
Scofield et al., "Nucleotide sequence of a member of the napin storage protein family from Bassica napus", The Journal of Biological Chemistry, vol. 262, No. 25, pp. 12202–12208, Sep. 5, 1987.
Simon et al., "Nucleotide Sequence of A cDNA Clone of Brassica napus 12S Storage Protein Shows Homology With Legumin From *Pisum sativum*", Plant Molecular Biology 5, pp. 191–201, 1985.
Guerche et al., "Direct Gene Transfer By Electroporation In *Brassica Napus*", Plant Science, 52 pp. 111–116, 1987.
Josefsson et al., "Structure of A Gene Encoding The 1.7 S Storage Protein, Napin, From *Brassica napus*", The Journal of Biological Chemistry, vol. 262, No. 25, pp. 12196–12201, Sep. 5, 1987.
Radke et al., "Transformation of *Brassica napus* L. Using *Agrobacterium tumefaciens:* Developmentally Regulated Expression of A Reintroduced Napin Gene", Theor. Appln. Genet 75: pp. 685–694, 1988.
Ryan et al., "Genomic Sequence of A 12S Seed Storage Protein From Oilseed Rape *Brassica napus* c.v. Jet Neuf)", Nucleic Acids Research, vol. 17, 1989, p. 3584.
Baszczynski et al. "Isolation And Nucleotide Sequence of A Genomic Clone Encoding A New *Brassica napus* Napin Gene", Plant Molecular Biology 14: pp. 633–635, 1990.
Kitamura, "Breeding Trials For Improving The Food–Processing Quality of Soybeans", Trends In Food Science & Technology, vol. 4, pp. 64–67, Mar. 1993.
Daussant et al., "Seed Proteins", Annual Proceedings of The Phytochemical Society of Europe, pp. 223–253, 1993.
Altenbach et al., "Accumulation of A Brazil Nut Albumin In Seeds of Transgenic Canola Results In Enhanced Levels of Seed Protein Methionine", Plant Molecular Biology 18: pp. 235–245, 1992.
Jaynes et al 1988 Trends in Biotech. 4: 314–320.
Altenbach et al 1989 Pl. Molec Biol 13: 513–522.
Ram et al 1987 In Proceedings World Conf on Biotechnology for the Fats and Oil Industry (Applewhite ed.) AOCS publisher, pp. 65–71.

*Primary Examiner*—Patricia R. Moody
*Attorney, Agent, or Firm*—Wenderoth, Lind & Ponack

[57] ABSTRACT

An oilseed crop with altered amino acid composition and/or fatty acid composition is provided. The crop is prepared by introducing antisense gene of a seed storage protein into the oilseed crop.

9 Claims, 2 Drawing Sheets

OILSEED CROPS PRODUCING VALUABLE SEEDS HAVING ALTERED AMINO ACID COMPOSITION AND FATTY ACID COMPOSITION

BACKGROUND OF THE INVENTION

1. Field of the Invention

The present invention relates to oilseed crops producing valuable seeds having altered amino acid composition and fatty acid composition, and to a method for preparing such crops. More specifically, the present invention relates to oilseed crops with an introduced antisense gene of seed storage protein and to a method for preparing such crops.

2. Description of Related Art

The term "oilseed crops" as used herein refers to crops which are used to obtain oils (fats) from their seeds. Such crops have been widely cultivated as sources for edible oils, such as a rapeseed oil and a sesame oil, or as sources for a variety of oils for industrial use. For example, Brassica plants, of which seeds include lipids at about 60% of the seed weight, are cultivated in various places in the world. The oilseed meals contain proteins at high level and have been used as feed and fertilizers.

However, a rapeseed oil has been known to contain an erucic acid, which is harmful to human, and oilmeal of Brassica species has been known to contain glycocynolates which are associated with toxic effects on livestocks. Therefore, a great effort had been made to lower the amount of such harmful components by conventional plant breeding. As the result, a "double low" variant has been developed in Canada, which contains erucic acid at less than 2% of the seed weight in its seed oil, and glycocynolate at less than 30 micromol per 1 g of meal.

Recently, oil consumption has increased and the associated market has become in need of diversity of oil. Accordingly, oilseeds with high lipid content and with valuable fatty acid compositions are needed for a variety of purposes. For example, as edible oil, oilseeds containing negligible erucic acid and low levels of saturated fatty acid are desired because such oils are good for human health. On the other hand, oilseeds containing large amounts of erucic acid, medium-chain fatty acid, and/or polyunsaturated fatty acid are desired for industrial purpose. As for meal, those including a large amount of proteins or essential amino acids are desired.

It is laborious to develop new desirous breeds and it is difficult to alter valuable components in seeds for specific purpose by conventional breeding methods with crossing. Conventional breeding with crossing comprises very laborious and time-consuming processes which aim at the selection of desired breeds from various variants and establishment of pure lines. Other methods, such as γ-ray irradiation and somaclonal variation, have been conducted in an attempt of obtaining desired breeds from various variants. However, breeds obtained by these methods often cannot be used for cultivation because, in addition to targeted genes, other genes in breeds are often mutated simultaneously.

On the contrary, methods involving gene engineering technique are advantageous for specifically preparing desired breeds, because such methods permit the alteration of a specific gene alone and introduction of the targeted gene into crops. In more detail, such methods comprise the steps of 1) isolating a gene encoding desired phenotype, 2) modifying the gene so that the gene is expressed in desired tissues or sites, and 3) introducing the gene into the crops to express the desired phenotype.

Examples of genes encoding targeted phenotype in the above step 1) include genes encoding enzymes involved in biosynthesis of seed storage compounds and genes of storage proteins. Seed storage comounds are essentially lipids, proteins, and carbohydrates, which vary in amount depending on plants. It is known that these compounds are accumulated during embryogenesis, and that the biosynthesis pathways of these compounds are closely related. In more detail, these compounds are synthesized from the same and identical starting substance. As for Brassica species, it is known that lipids and proteins are accumulated in seeds, but all enzymes involved in biosynthesis of storage lipids are not isolated. Genes for napin or cruciferin, which are storage proteins, have been isolated in Arabidopsis (Plant Phys., 87, 859–866, 1988; Plant Mol. Biol., 11, 805–820, 1988), *Raphanus sativus* (Plant Mol. Biol., 20, 467–479, 1992; Gene, 99, 77–85, 1991), *Brassica napus* (Plant Mol. Biol., 5, 191–201, 1985; Plant Mol. Biol., 14, 633–635, 1990), and the like.

The above step 2) is selection and construction of "DNA part", which is an antisense gene (antisense oligonucleotides) of a given storage protein and suppresses the expression of the gene and alters the phenotype of a crop, when introduced into the crop. As for *B. napus*, an example of expression of a chimeric gene consisting of DHFR gene and napin gene driven by the napin promoter has been reported (S. E. Radde, Theor. Appl. Genet., 75, 685–694, 1988), but no example of introduction of an antisense gene of a storage protein has been reported. As for introduction of antisense gene, there is a report that when antisense gene of ADP-glucose-pyrophosphorylase, one of the starch synthesizing enzymes in potato, has been introduced into potato, the amount of starch was decreased and the amount of sucrose and certain proteins were increased (EMBO J., 11, 1229–1238, 1992).

The above step 3) is a process for introducing a desired gene into a crop. As for *B. napus*, for example, there is known a method for regenerating plants from protoplasts introduced with the targeted DNA by electroporation (Plant Science, 52, 111–116, 1987). A method for regenerating a plant introduced with targeted DNA by Agrobacterium-mediated transformation is also known (Japanese Laid-Open Patent Publication No. 1-500718).

SUMMARY OF THE INVENTION

The present inventors made an extensive study for the purpose of increasing the amount of storage proteins and altering amino acids composition in oilseed crops, such as Brassica crop. As the result of the study, the inventors have found that the amino acid compositions in seeds of Brassica crop can be altered by introducing an antisense gene of a seed storage protein. Surprisingly, the inventors have also found that the fatty acid composition, and essential amino acid composition in seeds can be altered by introducing such an antisense gene. The present invention is based on such findings.

Thus, the present invention is directed to oilseed crops transformed with antisense gene of a seed storage protein, methods for preparing the transformed oilseed crops, recombinant vectors used in the method, and the seeds obtained from the transformed crops. The present invention is further illustrated in detail below.

As described above, any oilseed crops that can be used for extraction of oils (fats) from their seeds may be used in the present invention. The examples of oilseed crops include rapeseed, sesame, Tougoma (hima), Egoma, peanut, olive, soybean, maize, flax, sunflowers, and oilpalm. Preferable oilseed crops are rapeseed, soybean, and maize, and the most preferable crop is rapeseed in the present invention.

Seed storage proteins are not limited, but napin and/or cruciferin are preferable. These two proteins are major proteins in seeds of Brassica plant. About 20% and 60% of the total seed proteins in *B. napus* of rape are napin and cruciferin, respectively. Napin is the general term for 1.7S storage proteins synthesized by Brassica plant which include several proteins having partially different amino acid sequences. Genes encoding these proteins form a gene family consisting of twenty or more genes. The homologies of these genes between any two plants are 90% or move. Cruciferin is the general term for 12S storage proteins comprising four types of subunit pairs in *Brassica napus*. The homology of these genes encoding these four subunit pairs is lower than that of napin, and it is 40% or less even between two genes belonging to the same species.

In the present invention, antisense gene of such seed storage proteins are introduced into crops. Any antisense gene of a seed storage protein can be used. However, a DNA sequence having high homology with an endogenous gene of a target plant is preferable, because antisense RNA transcribed from the introduced antisense DNA may be efficiently hybridized with the transcript of the endogenous gene when they have high homology. Antisense genes may correspond to full length or a part of cDNA or genomic DNA of targeted genes. When napin antisense gene is used in the present invention, napin gene is first isolated by PCR method with the use of genomic DNA of *B. napus* or the like as a template. For example, napin gene and cruciferin gene can be amplified for isolation by PCR method by the use of genomic DNA of *B. napus*, based on the sequence ranging from ca 1111 bp to ca 1783 bp of napA base sequence reported by Rask L. (J. Biol. Chem., 262 12196–12201, 1986) in the case of napin gene, and based on the sequence ranging from 680 bp to 1278 bp of cruA base sequence reported by A. J. Ryan (Nuc. Acid Res., 17, 3584, 1989) in the case of cruciferin gene. PCR is the method to amplify a target DNA region by repeating the steps of heat denaturation of a template, annealing of primer and template, and elongation of DNA with the use of thermostable polymerase (Saiki, Science, 239, 487–491, 1988). In more detail, for example, genomic DNA can be isolated from leaves of *B. napus* cv. Westar or the like, according to the method described in Mol. Gen. Genet., 211, 27–34, 1988, and about 300 ng of the genomic DNA can be used as a template. The steps of heat denaturation of the template to dissociate single+strand and single−strand, annealing of primer and template, and synthesis of DNA with the use of thermostable polymerase are repeated 20 to 30 cycles to amplify the DNA complementary to the napin gene. The amplified DNAs correspond to 90% or more of napin transcription region and 25% of cruciferin transcription region.

Next, an expression vector containing an antisense gene is constructed. For example, an expression vector must contain a specific promoter so that the antisense gene is sufficiently expressed in *B. napus* seeds. Moreover, it is preferable to use an expression vector that can express antisense gene in the same time and in the same place as endogenous inherent gene encoding the storage protein, in order to lower the amount of the undesired protein efficiently. For example, when the antisense gene encoding napin is used to transform the crop, a promoter can be obtained by PCR method with the use of genomic DNA of *B. napus* or the like as a template, and oligonucleotides corresponding to sequences ranging from ca 1 bp to ca 1145 bp of the napA base sequence as a primer. Where antisense gene of cruciferin is used as insertion gene, the promoter region of cruciferin gene may be used, and the sequence ranging from ca 1 bp to ca 709 bp of the above-noted sequence of cruA may be amplified for use. It is important to confirm a function of the amplified promoter fragment by PCR before use because promoters of Pseudo genes are not available.

An expression vector may further contain a terminator in order to terminate the transcription of a gene efficiently and to stabilize a generated RNA. Any terminator that can function in a plant cell may be used. For example, the terminator for nopalin synthase gene NOS (pBI221, Jefferson, EMBO J., 6, 3901–3907, 1987) can be used.

Examples of methods for transforming plants include an Agrobacterium-mediated transformation, an electroporation, and the like. Plasmids of pLAN series (Plant Cell Rep., 10, 286–290, 1991) are preferable for the Agrobacterium-mediated transformation and plasmids of pUC series are preferable for the electroporation. These plasmids contain neomycin phosphotransferase gene and hygromycin phosphotransferase gene as a selection marker. Plasmids may further contain two or more exogenous genes selected from the group consisting of neomycin phosphotransferase gene, hygromycin phosphotransferase gene, chloramphenicol acetyltransferase gene, β-glucuronidase gene, and the like, and one of the exogenous genes is preferably used as a selection marker for selecting transformants. The most preferable selection marker is neomycin phosphotransferase. In an electroporation, a plasmid containing a selection marker gene and other exogenous gene, or two plasmids, one of which contains a selection marker gene and the other contains an other exogenous gene, can be used.

An oilseed crop with altered amount of seed storage proteins can be prepared by introducing such plasmids into hypocotyls or protoplasts of an oilseed crop.

Agrobacterium-mediated transformation may be carried out according to the process described in Japanese Laid-Open (Kohyo) Patent Publication 1-500718.

In an electroporation, protoplast derived from Brassica can be prepared as follows. A shoot that has been cultured in sterilized condition is treated with an isotonic solution comprising an enzyme to degrade cell walls e.g., cellulase, pectinase, or the like, at 25° to 30° C. for 5 to 20 hours. After treatment, the solution is filtered to remove undigested cells and the filtrate is centrifuged to obtain purified protoplast (Japanese Patent Application Ser. No. 4-276069). Before electroporation, $6 \times 10^5$ cells/ml of protoplast derived from *B. napus* cv. Westar and a DNA expression vector (e.g., 40 to 80 μg/ml) comprising napin antisense gene or cruciferin antisense gene and neomycin phosphotransferase gene (e.g. 40 to 80 μg/ml) are suspended in a liquid medium (e.g., buffer) containing 30 to 200 mM KCl, 0 to 50 mMMgCl, and 0.2 to 0.6 M mannitol. Then, the vector is introduced into the protoplast by an electric pulse. Preferable conditions for the electric pulse treatment is that 200 to 1000 V/cm primary voltage of direct current pulse obtained by 100 to 1000 μF condensor with about 1 to 30 msec pulse width is applied. The electroporated protoplasts can be suspended in, for example, KMmedium (Planta, 126, 105–110, 1975) containing 0.05 to 0.5 mg/l of 2, 4-dichlorophenoxy acetate (2,4-D), 0.02 to 0.5 mg/l of naphthalene acetate (NAA), 0.1 to 2.0 mg/l of benzylaminopurine (BAP), and 0.4M glucose, at $10^5$ cells/ml, and the mixture is cultured at 25° C. in the dark. After 3 to 4 weeks in culture, colonies with about 0.5 to 1 mmø can be formed. If the introduced plasmid contains neomycin phosphotransferase gene as a selection marker, 10 to 50 µg/ml kanamycin can be added after one week in culture to efficiently select transformed colonies. The colonies are transferred onto culture medium with 10 to 50 µg/ml kanamycin, for example, MS solid medium (Murashige and Skoog, 1962) containing 0.5 to 2 mg/l of 2, 4-D, 0.1 to 0.5 mg/l BAP, 1 to 5% sorbitol, 1 to 5% sucrose, 0.5 to 2 g/l casein hydrolysate (CH), and 0.5 to 1% agarose, and after 2 to 4 weeks at 25° C. in the light (1000 to 4000 lux) 3 to 5 mmø green calli are obtained. The obtained calli are then cultured in a culture medium free from kanamycin, for example, MS solid medium containing 0.01 to 0.1 mg/l NAA, 0.5 to 2 mg/l BAP, 1 to 5% sorbitol, 0.5 to 2% sucrose, 0.05 to 0.5 mg/l CH, and 0.5 to 1% agarose, at 25° C. in the light (1000 to 4000 lux) to obtain a regenerated shoots. The regenerated shoots are then cultured in a culture medium for root-induction, for example, MS solid medium containing 0.05 to 0.2 mg/l NAA, 0.01 to 0.05 mg/l BAP, 1 to 5% sucrose, and 0.2% Gellight (Kelco, Division of Merck and Co., Inc.).

Genomic DNA can be isolated from the leaves of the regenerated plants according to the method described in Mol. Gen. Gent., 211, 27–34, 1988. The resulting 300 ng of genomic DNA is amplified by PCR to select a transformant containing antisense gene of a seed storage protein. When a napin antisense gene is introduced into Brassica plants, primers corresponding to the sequence from position 1 to 19 bp of napA gene (supra) and the sequence from position 1579 to 1595 bp of NOS terminator (5'- GCATGACGT-TATTTATG-3', pCaMVNEO; Fromm et al., Nature, 319, 791–793, 1986, SEQ ID NO:5) are used for PCR survey. When a cruciferin antisense gene is introduced, primers corresponding to the sequence from position 1 bp to upstream 18 bp of cruA gene (supra) and part of NOS terminator and used.

After acclimation of regenerated plant containing antisense gene of a seed storage protein, the plant is cultivated in a greenhouse. The transgenic plants produce seeds after 3 to 6 months cultivation. The existence of an introduced gene can be confirmed by a Southern blot analysis (Southern, J. Mol. Biol., 98, 503–517, 1975). For example, 10 µg of genomic DNA prepared according to the method of Wolbot et al. (Mol. Gen. Gent., 211, 27–34, 1988) is digested with appropriate restriction enzyme(s) in 100 µl of reaction mixture (TOYOBO Co.). The resulting solution is ethanol precipitated. The obtained precipitate is washed with 70% ethanol, dried, and dissolved in 10 µl distilled water. To the resulting solution, 2 µl dye (Molecular Cloning) is added. The solution is then electrophoresed by the use of 0.8% agarose gel (FMC SEAKEM GTG AGAROSE, TBE buffer). Separated fragments are subjected to partial hydrolysis with acid, and alkaline denatured according to the method described in Direction of Amersham Hybond N Membrane so that the fragments are transferred onto hybond N membrane. The membrane is prehybridized in 50% formamide,×4 SSCP (Molecular Cloning), 1% SDS, 0.5% skim milk, 0.25 mg/ml bovine sperm DNA for more than one hour at 42° C. Probe can be obtained as follows. Plasmid that is used to transform protoplast is digested with appropriate restriction enzyme(s) as described above. The resulting solution is ethanol precipitated. The obtained precipitate is washed with 70% ethanol, dried, and dissolved in 5 µl distilled water. To the resulting solution, 1 µl dye (Molecular Cloning) is added. The solution is then electrophoresed with the use of 0.8% agarose gel (FMC SEAKEM GTG AGAROSE, TBE buffer) to recover a DNA fragment containing antisense gene or a partial fragment thereof (Molecular Cloning). The obtained fragment is used as a probe. The DNA fragment (25 ng) is labeled with $[\alpha^{32}P]dCTP$ with the use of multiprime labeling kit (Amersham). Heat denatured DNA fragment (probe) is added to a hybridization solution (0.1 g dextran sulfate/ml prehybridization solution). The above-mentioned prehybridized membrane removed from prehybridization solution is immersed in a hybridization solution and allowed to stand overnight at 42° C. The membrane is then treated in 100 ml of 2×SSC+0.1% SDS for 15 min.×2 with shaking, washed with 100 ml of 0.1×SSC+ 0.1% SDS for 15 min.×2, and subjected to an autoradiography to detect bands that specifically hybridized with the probe.

The expression of antisense gene of a seed storage protein can be confirmed by SDS polyacrylamide gel electrophoresis (SDS-PAGE) of total proteins of the seeds extracted by a standard method. For example, the total protein is first extracted in 100 µl/seed sample buffer (62.5 mM Tris-HCl pH 6.8, 2% SDS, 10% glycerol, 5% 2-mercaptoethanol, 0.0001% Bromophenol Blue) and then 15 µg of the protein is fractionated by SDS-PAGE (Nature, 227, 680–685, 1970). The resulting gel is stained with a solution of 0.25% Coomassie Brilliant Blue, 45% ethanol, and 10% acetic acid and then immersed in a decolorizing solution containing ethanol, acetic acid, and water (25:8:65). When a napin antisense gene is used to transform B. napus, the bands corresponding to α chain and β chain of napin can be detected at 4 kD and 9 kD, respectively. When a cruciferin antisense gene is introduced, the bands corresponding to 3 or 4 α chains of and 3 or 4 β chains of cruciferin subunit pair can be detected at about 20 kDa and about 30 kDa, respectively. The amount of napin or cruciferin can be deduced by comparing the depth of the resulting bands with those obtained from a non-transformed plant, thereby degree of expression of antisense gene of napin or cruciferin can be confirmed.

In accordance with the procedure mentioned above, there is obtained oilseed crops of the invention in which amino acid composition and/or fatty acid composition have been improved nutritionally. For instance, nutritious oilseed crops of the invention can be obtained in which the contents of unsaturated fatty acids such as linoleic or linolenic acid, and essential amino acids such as lysine, methionine or cysteine have been increased.

The present invention is further illustrated by the following examples. The examples are representative only and should not be construed as limiting in any respect.

DETAILED DESCRIPTION OF THE PREFERRED EMBODIMENT(S)

EXAMPLE 1

Figure 1:
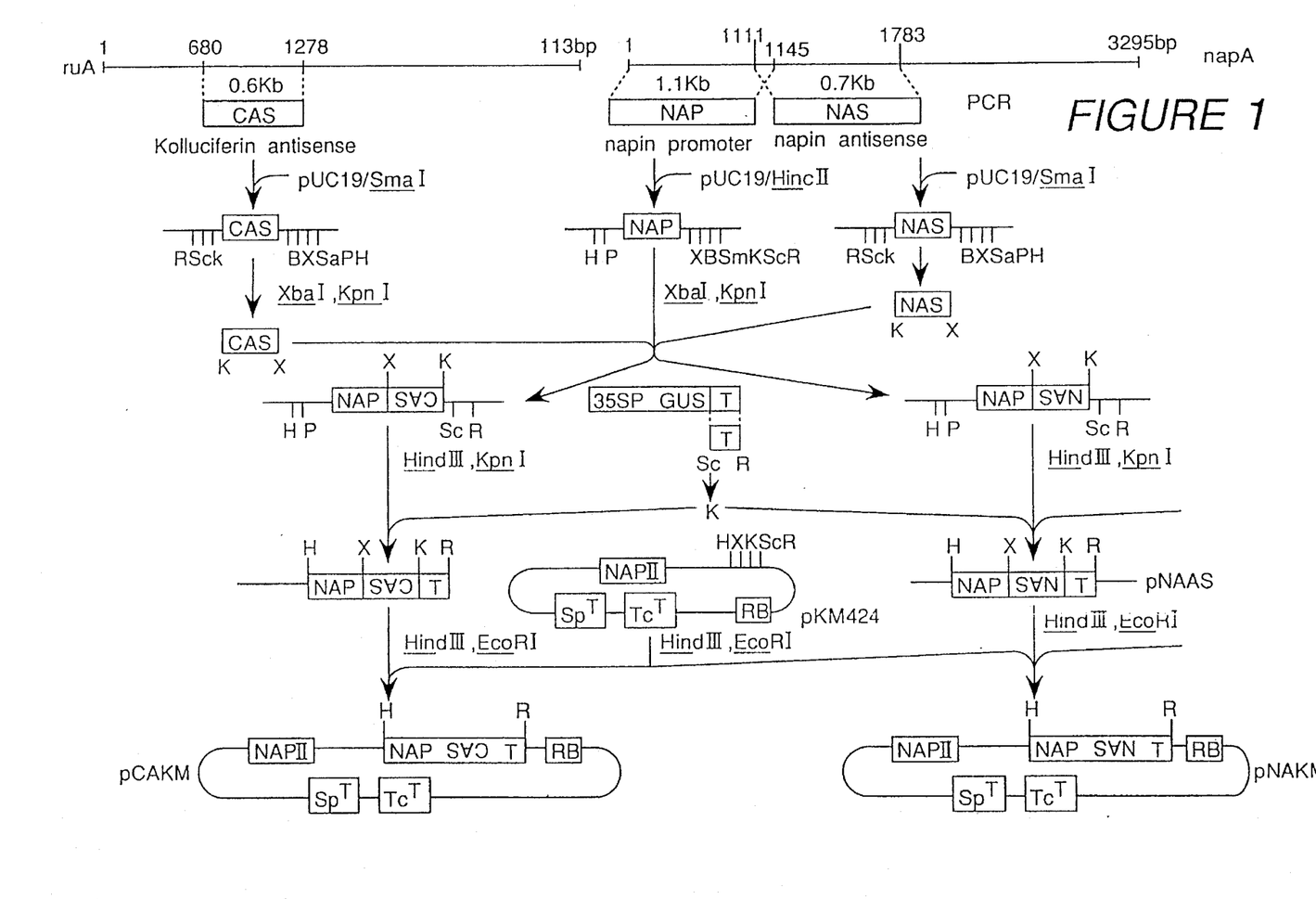
FIG. 1 represents the construction of the vectors prepared in Examples 1 and 8.

Construction of vector pNAKM (FIG. 1)

A napin promoter region and a part of the napin gene were amplified by PCR with the use of primers based on the sequence of napA gene (J. Biol. Chem., 262, 12196–12201, 1987). First, genomic DNA was extracted from leaves of B. napus cv. Westar by CTAB method (Focus, 12, 13–15, 1989). In more detail, an appropriate amount of liquid nitrogen was added to about 5 g of the leaves in a mortar and the leaves were crushed with a pestle. Then, 15 ml of DNA extraction solution (2% CTAB, 1.4M NaCl, 0.2% 2-mercaptoethanol, 20 mM EDTA, and 100 mM Tris-HCl (pH 8)) was added and the leaves were further crushed. The extract was transferred to a polypropylene tube and allowed to stand for more than one hour at 65° C. with occasional shaking. The equal volume of a solution containing phenol (saturated with 10 mM Tris-HCl (pH 8) and 1 mM EDTA), chrolofrom, and isoamyl alcohol (25:24:1) was added to the extract and mixed. The mixture was centrifuged for 15 min. at 15000 rpm (KUBOTA, KR-20000T). The supernatant was transferred to another tube and ⅔ volume of isopropanol was added. The mixture was allowed to stand for more than 30 min. at room temperature and centrifuged for 20 min. at 14000 rpm. The supernatant was removed to obtain precipitate. An appropriate amount of 70% ethanol was added to wash the precipitate and then the precipitate was dried. The precipitate was dissolved in 750 µl TE (10 mM Tris-HCl (pH 8.0) and 1 mM EDTA) containing 1 g/ml cesium chloride. One drop of 10 mg/ml ethidium bromide was added to the solution and the solution was centrifuged overnight at 100000 rpm (BECKMAN, TL-100). Band-fractions were recovered, treated with n-butanol to remove ethidium bromide, transferred in a dialytic membrane (Sanmitsu Pure chemicals) and desalted in water. To the resulting solution in the dialytic membrane, 2.5 volumes of ethanol was added in the presence of 30 mM sodium acetate, and the mixture was centrifuged for 15 min at 15000 rpm at low temperatures to recover genomic DNA. The recovered DNA was dissolved in TE solution to obtain 1 µg/ml DNA solution.

The genomic DNA (300 ng) was used for amplification of a napin promoter region and a napin coding region by PCR. As primers the sequence from position 1 to 19 bp of napA gene (J. Biol. Chem., 262, 12196–12201, 1987) (5'-AAGCTTTCTTCATCGGTGA-3': SEQ ID No.1) and the complementary sequence to 21 bp from position 1125 to 1145 bp of napA gene (5'-CAAGATTAAAAACATACACGA-3': SEQ ID No.2) are used for amplifying a napin promoter region, and as primers the sequence from position 1111 to 1131 bp of napA gene (5'-CTCATCAATACAAACAAGAT-3':SEQ ID No.3), and the complementary sequence to 20 bp from position 1763 to 1783 bp of napA gene (5'-TATGTAAGGTTTTATCTAGG-3': SEQ ID No. 4) are used for obtaining napin coding region. PCR was performed by the use of DNA Thermal Cycler (Perkin Elmer Cetus) in a mixture prepared by the protocol of Gene-Amp Kit of the above company.

To obtain a napin promoter region, 30 cycles were done with 100 µl of reaction mixture, one cycle consisting of a denaturation step at 94° C. for a minute, an annealing step at 52° C. for 2 min, and an extension step with thermostable polymerase at 72° C. for 3 min. To obtain a napin coding region, 30 cycles were done, one cycle consisting of a denaturation step at 94° C. for a minute, an annealing step at 50° C. for 2 min, and an extension step with thermostable polymerase at 72° C. for 3 min. The reaction mixture (1/20 volumes) was analyzed with agarose gel electrophoresis to detect bands. A band at 1.1 kb corresponds to a promoter and a band at 0.7 kb corresponds to a napin coding region.

The DNA fragments (1.1 kb and 0.7 kb) were ethanol precipitated individuary cloned in HincII and SmaI sites of pUC plasmid, respectively (pNap, pNAS).

Then, the resulting pNAS (10 µg) was digested with XbaI and KpnI in buffer (100 µl, TOYOBO) for 3 hours at 37° C., fractionated by 1% Seakem GTG agarose (FMC) gel electrophoresis with the use of 1×TBE buffer (Molecular Cloning, Maniatis) (MUPID, Cosmobio, 100 V, 30 min). Then the gel was strained with 0.5 µg/l ethidium bromide and the band corresponding to a napin coding region was extracted. The band-fraction was transferred to a dialytic membrane and subjected to electrophoresis for an hour at 4° C. at 120 mA to recover DNA. An equal volume of phenol was added to the recovered DNA and the mixture was shaked to obtain two-layered solution. The aqueous phase was recovered and the phase was further treated with chloroform to purify the DNA fragment. The DNA fragment was then ethanol precipitated and dissolved in 5 µl water. The resulting solution (1 µl) and a 2 µl solution including napin promoter prepared by the same method above from pNap⁻ were ligated at 4° C. overnight in TAKARA ligation kit reaction mixture (30 µl).

The mixture containing ligated plasmid DNA (10 µl) was used to transform an E. coli competent cell DH5α (BRL) (Inoue, Gene, 96, 23–29, 1990). Colonies of transformants containing the plasmid were selected on LB agarose medium containing 50 µg/ml ampicillin (Molecular cloning). DNA was prepared from culture liquid (1 ml) containing the selected colonies (LB medium) by an alkaline SDS method (Molecular Cloning). The DNA (1/50 volumes) was digested with 1U of HindIII and KpnI (TOYOBO) in 10 µl reaction mixture containing RNase 0.5 µg/ml for 30 min at 37° C. After fractionation of the digested DNA by gel electrophoresis, the clone showing 1.8 kb fragment on the gel was selected. The clone contained a plasmid having a portion of napin gene ligated with the napin promoter in a reverse direction.

The terminator derived from NOS region in pBI221 (TOYOBO) was used.

Plasmid pBI221 (10 µg) was digested with SacI in a buffer (120 µl, TOYOBO) overnight at 37° C. The resulting DNA fragment was purified with phenol and chloroform, ethanol precipitated, and dissolved in 20 µl of water. The solution (8 µl) was treated with 10 µl solution of TAKARA blunting kit (TAKARA) to obtain a blunt-ended DNA fragment. The blunt-ended DNA fragment was dissolved in 5 µl of water and 2 µl of the solution was mixed with 1 µl of solution containing KpnI linkers (TOYOBO) to ligate the blunt-ended DNA fragment and the linkers by the use of a TAKARA ligation kit. DNA fragment linked with KpnI linkers was further purified, recovered, and dissolved in 5 µl of water. The resulting solution was treated with EcoRI and KpnI to obtain a DNA fragment comprising the vector portion and terminator portion from NOS.

The DNA fragment (0.1 µg) thus obtained and a DNA fragment having a portion of a napin antisense gene fused to the napin promoter were ligated to obtain plasmid pNAAS. This plasmid was used to transform protoplasts by electroporation.

A plasmid that can be used for Agrobacterium-mediated transformation was constructed as described below. Plasmid pKM424 containing tetracycline resistant gene and spectinomycin resistant gene as E. coli selection markers and nopaline resistant gene as a plant selection marker (Plant Cell Rep., 10, 286–290, 1991), which was prepared from pLAN421 by substituting a multiple cloning site for a structural gene ($35S^P$-GUS-$NOS^T$), was digested with HindIII and EcoRI. The digested plasmid was treated with phenol and ethanol precipitated to purify the DNA. pNAAS plasmid was treated with the same enzymes to obtain a DNA fragment containing a napin promoter and napin antisense gene. The prepared DNA fragment from pLAN421 and the DNA fragment containing napin antisense gene were ligated to obtain pNAKM.

The resulting plasmid was used to transform *Agrobacterium tumefaciens* EHA101 strain. A single colony of EHA101 was cultured in YEB medium (0.1% Yeast extract, 0.5% Beef extract, 0.5% peptone, and 0.5% sucrose (pH7.0)) overnight. The culture (1 ml) was added to a fresh YEB medium containing 25 µg/ml kanamycin (Km), 12.5 µg/ml chloramphenicol (Cm), 25 µg/ml spectinomycin (Sp), and 1 µg/ml tetracycline (Tc) and cultured for 5 to 6 hours at 30° C. The resulting culture was centrifuged for 5 min at 4000 rpm. To the resulting precipitate, 20 ml of 10 mM Tris-HCl (pH 8) was added to wash the precipitate. The precipitate was suspended in 400 µl YEB medium and 90 µl of the suspension was mixed with 10 µl solution containing 10 ng pNAKM and allowed to stand for 5 min at −110° C. and for 25 min at 37° C. To the resulting solution, 400 µl of YEB medium was added and the mixture was cultured at 30° C. overnight. The resulting culture (50 µl) was plated on YEB agarose medium containing 50 µg/ml kanamycin (Km), 25 µg/ml chloramphenicol (Cm), 50 µg/ml spectinomycin (Sp), and 2 µg/ml tetracycline (Tc) and cultured two overnights at 30° C. to select colonies containing plasmids (DNA Cloning). DNA was prepared from YEB culture medium containing one of the colonies by an alkaline SDS method (Molecular Cloning) and the obtained DNA was digested with 1 U of HindIII and EcoRI (TOYOBO) in 10 µl of reaction mixture containing 0.5 µg/ml RNase for 30 min at 37° C. After gel electrophoresis of the mixture the clone showing 2.1 kb band on the gel was selected.

EXAMPLE 2

Transformation, selection and regeneration of callus carrying napin antisense gene Seeds of *B. napus* cv. Westar were treated with 10% hydrogen peroxide solution for 25 min and dried. The treated seeds were cultured on MS agarose medium in the light (1000 to 4000 lux) for 2 to 3 weeks. The sterilized hypocotyls were cut in 2 to 5 mm length, put on preculture medium (B5-Vitamin; Gamborg et al., Exp. Cell. Res., 50, 151–158, 1968), and cultured overnight in a light place. The preculture medium contained MS agarose medium containing 1 mg/l 2,4-D, 3% sucrose, and 0.7% agarose covered with tobacco culture cells BY-2 under sterilized filter paper thereon. A single colony of Agrobacterium carrying a pNAKM plasmid was cultured in YEB liquid medium (5 ml) with antibiotics at 30° C. overnight. The culture was centrifuged for 10 min at 3000 rpm and the precipitate was washed once with MS liquid medium containing 3% sucrose and then suspended in the same MS medium. To the suspended liquid containing Agrobacterium, the precultured hypocotyls were added and shake-cultured for 5 to 20 min at 25° C. The resulting solution was filtered with sterilized paper towel to remove an excess amount of Agrobacterium and recover hypocotyls. The hypocotyls were then cultured on the above-mentioned preculture medium three overnights to infect hypocotyls with Agrobacterium. Then, the infected hypocotyls were transferred on an elimination medium (MS agarose medium including B5-Vitamin, 1 mg/l 2,4-D, 3% sucrose, 0.7% agarose, and 500 mg/l carbeniciline (Cb)) and cultured for 3 days to inhibit the growth of Agrobacterium.

Then the hypocotyls were transferred onto a first selection medium (MS agarose medium containing B5-Vitamin, 3 mg/l BAP, 1 mg/l zeatin, 2% sucrose, 0.7% agarose, 30 mg/l Km, and 500 mg/l Cb) and cultured for 2 weeks. As the result, only transformed plant cells carrying pNAKM plasmid were grown and green calli were formed.

Moreover, the hypocotyls were transferred onto a second selection medium (MS agarose medium containing B5-Vitamin, 3 mg/l BAP, 1 mg/l zeatin, 1% sucrose, 0.7% agarose, 30 mg/l Km, and 500 mg/l Cb) and cultured for 3 weeks. As the result, transformed calli were further grown. Then, only each callus portion was transferred onto a medium for germination (MS agarose medium containing B5-Vitamin, 3 mg/l BAP, 1 mg/l zeatin, 1% sucrose, 0.7% agarose, and 250 mg/l to 500 mg/l Cb). Regenerated shoots were cultured in medium for cell elongation (B5 agarose medium containing 0.1 mg/l BAP, 250 mg/l Cb, and 0.7% agarose) and then transferred onto medium for rooting, and acclimation.

Genomic DNAs were prepared from the regenerated plants and subjected to PCR survey with the primers corresponding to sequences of the introduced plasmid to select transgenic plants containing napin antisense gene. Genomic DNA was prepared as follows according to the method of Mol. Gen. Genet., 211, 27–34, 1988. 50 to 100 mg of kanamycin-resistant plants were crushed in a buffer (15% sucrose, 50 mM Tris-HCl (pH 8), 50 mM NaEDTA, and 500 mM NaCl) and nuclear fraction was separated by centrifugation. The precipitate was treated with a detergent solution (1.5% SDS, 20 mM Tris-HCl (pH 8), and 10 mM EDTA) and solved nuclear components were precipitated with 0.6 volumes of isopropanol to obtain nucleic acids. The nucleic acids were washed with 70% ethanol and dried to obtain genomic DNA. The DNA (300 ng) was subjected to PCR. Oligonucleotides from position 1 to 19 bp of napin promoter (SEQ ID:No. 1) and oligonucleotides complementary to the sequence from position 1579 to 1595 bp of NOS terminator (SEQ ID:No. 5:pCaMVNEO; Fromm, Nature, 319, 791–793, 1986) were used as primers. The PCR reaction comprised a denaturation step for a minute at 94° C., an annealing step for 2 min at 45° C., and an extension step for 3 min at 72° C. After PCR amplification, 10 µl of the reaction mixture was analyzed by an agarose gel electrophoresis to detect amplified bands. Transformed plants which were confirmed to integrate the introduced gene by PCR survey were cultivated in pots. Three to six months later, seeds were produced.

EXAMPLE 3

Detection of the expression of napin antisense gene in matured seeds

To a half of a matured seed, 100 µl of a sample buffer for protein extraction (62.5 mM Tris-HCl (pH 6.8), 2% SDS, and 10% glycerol) was added. The seed was crushed in the buffer and the mixture was centrifuged. A portion of the supernatant (corresponding to 15 µg of proteins) was fractionated by SDS-PAGE according to molecular weights. The resulting gel was stained with Coomassie Brilliant Blue and then decolorized too examine the amount of napin. The change of the amount of napin was determined by measuring the change of relative value between the band of napin and the band of another protein, e.g., cruciferin by imaging analysis (imaging analysis system, MKSIPS). If the amount of napin decreases, the value of the amount of the napin band/the amount of cruciferin band was lowered. The remaining half of the seed was germinated on a medium for seeding (MS agarose medium including 3% sucrose). Genomic DNA was prepared from the germinated seedling and analyzed by PCR survey as described in Example 2. It was confirmed that the introduced gene was inherited to the following generation. The decrease of the amount of napin correlated with the existence of the introduced gene. Table 1 shows the relationships of the result of an imaging analysis on SDS-PAGE and the existence of the introduced gene confirmed by PCR survey. Westar 1 to 8 are controls obtained from non-transformed matured seeds of *B. napus* cv. Westar treated by the same manner as the transformed seeds.

TABLE 1

| No. of seed | | Napin | cruciferin | napin/cruciferin | PCR |
|---|---|---|---|---|---|
| Westar | 1 | 8428 | 7066 | 1.2 | – |
| | 2 | 11047 | 4367 | 2.5 | – |
| | 3 | 17365 | 7190 | 2.4 | – |
| | 4 | 14117 | 7137 | 2 | – |
| | 5 | 21477 | 5955 | 3.6 | – |
| | 6 | 13980 | 6678 | 2.1 | – |

Seven half-cut seeds with decreased amount of napin determined by SDS-PAGE were homogenized in an appropriate amount of ice-cold acetone. The mixture was centrifuged and the precipitate was dried. Then, 200 µl of 70% formic acid was added to the dried precipitate to dissolve proteins. After centrifugation, 50 µl of supernatant was removed, dried, and hydrolyzed for 24 hours in the presence of HCl vapor and nitrogen at 110° C. To the resulting hydrolysate, 100 µl of citric acid buffer was added and the mixture was centrifuged. The supernatant (20 µl) was subjected to an amino acid analysis. Mature seeds derived from non-transformed *B. napus*. cv. Westar were also treated in the same manner and the amino acid compositions thereof were analyzed as controls. The test result showed that the amino acid composition of proteins in transformed seeds was altered and close to that pre-estimated, assuming that the decrease of napin content was compensated by the increase of cruciferin content. Table 2 shows the amino acid composition of proteins in transformed seeds, wherein amino acids are represented by one-letter symbols.

TABLE 2

| | Amino Acid Composition Analysis | | | | | | | | | | | | | | | | | |
|---|---|---|---|---|---|---|---|---|---|---|---|---|---|---|---|---|---|---|
| | B | T | S | Z | G | A | C | V | M | I | L | Y | F | K | H | R | P | A.A. % |
| Westar | 7.3 | 4.7 | 5.1 | 20 | 9.3 | 7.3 | 0.6 | 6.9 | 1.5 | 4.2 | 7.7 | 1.4 | 3.7 | 5.8 | 2.7 | 4.7 | 7.6 | 23.1 |
| Transformant | 9.4 | 5.1 | 5.4 | 18.4 | 10 | 7.1 | 0.3 | 7 | 1.4 | 4.5 | 7.9 | 1.6 | 3.8 | 4.9 | 2.3 | 4.8 | 6 | 24.1 |
| % | 129 | 109 | 106 | 92 | 108 | 97 | 50 | 101 | 93 | 107 | 103 | 114 | 102 | 84 | 85 | 102 | 79 | 104 |
| estimated % | 125 | 89 | 100 | 88 | 108 | 103 | 44 | 108 | 100 | 111 | 116 | 114 | 111 | 80 | 89 | 104 | 83 | 100 |

%: Transformant/Westar
estimated %: amino acid composition estimated assuming that cruciferin was substituted for all of the decreased napin.

TABLE 1-continued

| No. of seed | | Napin | cruciferin | napin/cruciferin | PCR |
|---|---|---|---|---|---|
| | 7 | 1124 | 3296 | 3.4 | – |
| | 8 | 6922 | 4725 | 1.5 | – |
| Transformant | 1 | 7150 | 7938 | 0.9 | + |
| | 2 | 1892 | 8554 | 0.2 | + |
| | 3 | 0 | 6526 | N.C. | + |
| | 4 | 13499 | 5217 | 2.6 | + |
| | 5 | 0 | 6448 | N.C. | + |
| | 6 | 7710 | 3791 | 2 | – |
| | 7 | 1404 | 8261 | 0.2 | + |
| | 8 | 365 | 10519 | 0.03 | + |
| | 9 | 2842 | 7232 | 0.4 | + |
| | 10 | 1324447 | 4396 | 3 | – |

N.C. = not counted

EXAMPLE 4

Determination of the total protein content in mature seed

Figure 2:
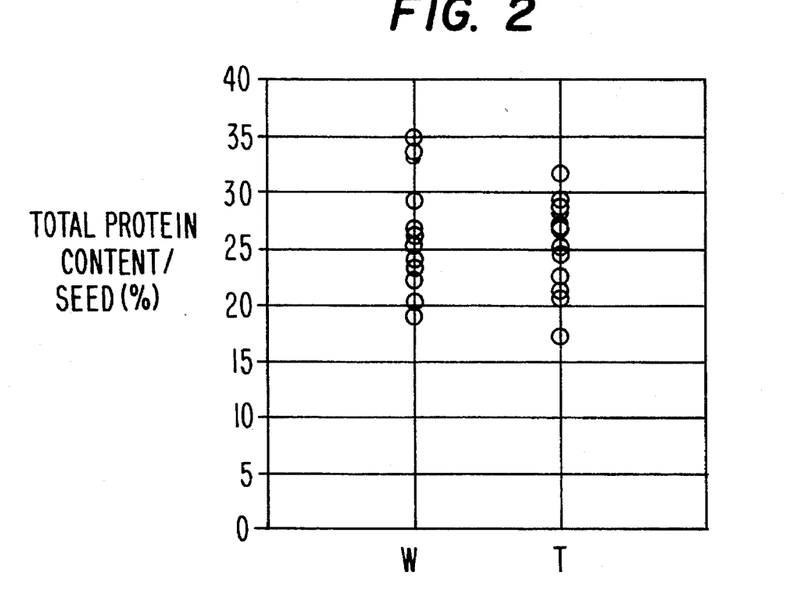
FIG. 2 represents the amount of total seed proteins, wherein W represents naturally-occurring seeds, B. napus cv. Westar and T represents transformed seeds.

The amount of the total seed protein extracted in Example 3 was determined by the use of Bio-Rad Protein Assay Kit (Bio-Rad Labs.). To 799 µl of distilled water, 200 µl of reagent was added. 1 µl sample was then added and the mixture was allowed to stand for 30 min at a room temperature. The absorbance of the solution was determined at 595 nm. The result showed that there is no correlation between decreasing napin content and the total protein content (FIG. 2).

EXAMPLE 5

Analysis of amino acid composition of mature seed protein

EXAMPLE 6

Figure 3:
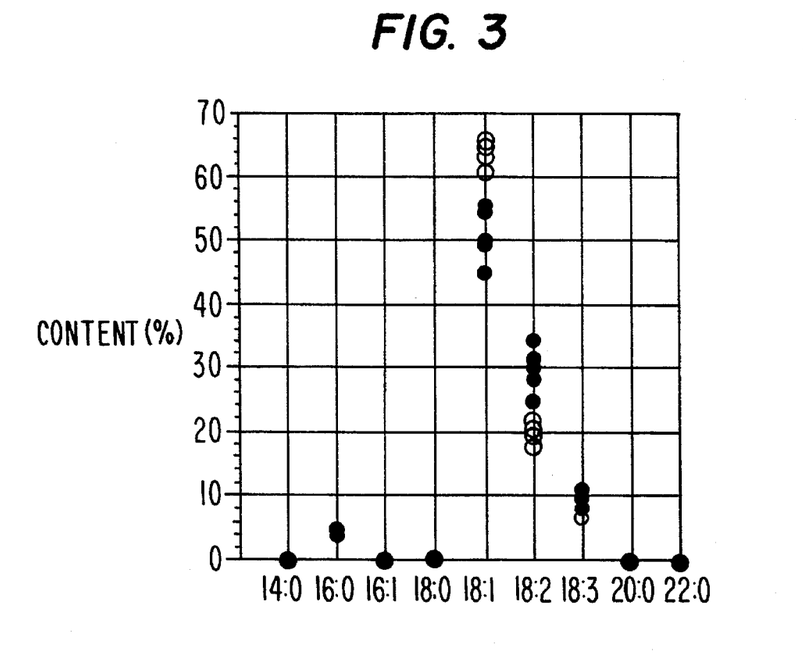
FIG. 3 represents the fatty acid composition in seeds wherein o represents naturally-occurring seeds, B. napus cv. Westar and ● represents transformed seeds.

Analysis of the total fatty acid content and fatty acid composition in mature seeds Ten half-cut seeds with decreased amount of napin determined by SDS-PAGE were homogenized in 5 ml of chloroform and methanol (3:1). The supernatant was transferred to a centrifuge tube. This procedure was repeated for three times and all of the supernatant was collected and allowed to stand for 20 min at room temperature. To the supernatant, 5 ml of distilled water and 5 ml of chloroform were added and the mixture was centrifuged for 20 min at 4° C. at 3000 rpm. The lower layer was transferred to a flask and evaporated at 30° C. while adding an appropriate amount of ethanol. To the evaporated extract, 50 nmol methyl pentadecanoate ($C_{15:0}$) and 2 ml of 2.5% sulfuric acid in methanol were added, and methylation reaction was done for 2 hours at 80° C. Then, 2 ml of hexane was added, and the mixture was stirred and allowed to stand. The upper layer, hexane layer, was transferred to another tube and dried in vacuum (Theor. Appl. Genet., 80, 241–245, 1990). Then, 100 µl of hexan was added. The resulting mixture (2 µl) was subjected to a fatty acid analysis by gas chromatography (GC-9A, Shimadzu Co.; 50 m×0.25 mmø×0.25 µM film Cyanopropyl 23 column, TOYO KASEI KOGYO Co. 185° C. 1 ml/min He;Injector, 200° C.). Fatty acid was also extracted from five seeds of non-transformed *B. napus* cv. Westar and used as a control. Fatty acid composition of the transgenic seeds was compared with that of the control. The result indicated that the total fatty acid content of transgenic seeds was the same as that of the control and that the amount of oleic acid was decreased and the amounts of linoleic acid and linolenic acid were increased in the transgenic seeds (FIG. 3).

EXAMPLE 7

Detection of the expression of napin antisense gene in a descendant plant

The seeds (T₁ generation) produced by the regenerated plant in Example 2 (T₀ generation) were germinated and the new seeds were obtained (T₂ generation). The amount of napin in the new seeds was determined as described in Example 3. The fatty acid composition of the seeds was also determined as described in Example 5. The results indicated revealed that the introduction of a cruciferin antisense gene resulted in the amino acid composition of total protein and increase of the contents of essential amino acids such as cysteine, methionine, and lysine. Table 3 shows the amino acid analysis of the seeds which have been subjected to transformation.

TABLE 3

| | Amino Acid Composition Analysis | | | | | | | | | | | | | | | | |
|---|---|---|---|---|---|---|---|---|---|---|---|---|---|---|---|---|---|
| | B | T | S | Z | G | A | C | V | M | I | L | Y | F | K | H | R | P |
| Westar | 7.7 | 4.5 | 4.5 | 17.6 | 8 | 7.1 | 6.2 | 5.8 | 1.2 | 3.9 | 7.4 | 0.5 | 3.6 | 4.8 | 2.7 | 5.1 | 7.4 |
| Transformant | 6.3 | 4.5 | 4.4 | 17.9 | 7.5 | 6.7 | 10.8 | 6 | 1.3 | 3.7 | 6.9 | 0.4 | 3.2 | 5.3 | 2.9 | 4.5 | 7.8 |
| (%) | 82 | 100 | 98 | 102 | 94 | 94 | 132 | 103 | 108 | 95 | 93 | 80 | 89 | 110 | 107 | 88 | 105 |

%: Transformant/Westar that the amount of napin was also decreased and the amount of oleic acid was decreased and the amounts of linoleic acid and linolenic acid were increased in T₂ seeds.

EXAMPLE 8

Construction of vector (pNACRU) (FIG. 1), transformation, selection of callus into which a cruciferin antisense gene has been introduced, and expression.

Part of cruciferin gene was isolated on the basis of the sequence of cruA gene (Nuc. Acid Res., 17 3584, 1989) in accordance with the afore-mentioned PCR method. For this purpose, the procedure employed in the isolation of part of napin gene was repeated except that sequence of 21 bases ranging from 680 to 700 bp of cruA gene (5'-AAAAAC-CACAACAACTAAGTA-3'; SEQ ID NO:6) and the complementary sequence to 18 bases ranging from 1261 bp to 1278 bp (5'-CACTGATGAGTCCTGGAA-3'; SEQ ID NO:7) were used as primers for cruciferin coding region. Cruciferin coding region gives a band at about 0.6 Kb. The DNA corresponding to this band was recovered and cloned in the plasmid pUC 19 at Sma I site (pCAS). After pCAS (10 ng) was treated in the same manner as napin gene, the cruciferin coding region was excised and inserted between napin promoter and NOS terminater in antisense orientation. The resultant plasmid was used when transformation was performed by electroporation. The plasmid used for Agrobacterium mediated transformation was prepared in the following manner: DNA fragment comprising napin promoter, cruciferin antisense gene and NOS terminator from the plasmid pCRAS was liked to pKM24 at Hind III and Eco RI sites (pCAKM). The resultant plasmid was used for the transformation into *Agrobacterium tumefacience* EHA101 in the method as previously mentioned. The transformation, selection of callus with introduced cruciferin antisense gene, and regeneration were performed in the same manner as in Example 2 except that the sequence ranging from 1 bp to upstream 18 bp (SEQ ID NO: 7) of cruciferin coding region and the complementary sequence to 17 bases ranging from 1579 bp to 1595 bp of NOS terminater (supra) were used as primers for PCR survey.

EXAMPLE 9

Analysis of amino acid composition of proteins in matured seeds.

Eight half-cut seeds with decreased amount of cruciferin determined by SDS-PAGE were subjected to amino acid analysis in the same manner as Example 5. The analysis According to the present invention, it is possible to alter an amino acid composition and fatty acid composition in seeds of oilseed crops. Specifically, the present invention provides oilseed crops producing high nutritious seeds having desired fatty acid composition and/or amino acid composition, such as the seeds having decreased amount of oleic acid increased amount of linoleic acid and linolenic acid, or the seeds having increased amount of essential amino acids such as lysine, methionine, and cysteine.

What is claimed is:

1. A rapeseed plant transformed with an antisense gene for cruciferin storage protein, which produces a seed containing an increased amount of lysine, methionine, and cysteine as compared with a seed produced by a rapeseed plant before transformation.

2. A rapeseed plant transformed with an antisense gene for napin storage protein, which produces a seed in which the fatty acid composition has been altered as compared with a seed produced by a rapeseed plant before transformation.

3. A rapeseed plant of claim 2 transformed with an antisense gene for napin storage protein, which produces a seed in which the fatty acid composition has a decreased amount of oleic acid as compared with a seed produced by a rapeseed plant before transformation.

4. A rapeseed plant of claim 2 transformed with an antisense gene for napin storage protein, which produces a seed in which the fatty acid composition has an increased amount of linoleic acid as compared with a seed produced by a rapeseed plant before transformation.

5. A rapeseed plant of claim 2 transformed with an antisense gene for napin storage protein, which produces a seed in which the fatty acid composition has an increased amount of linolenic acid as compared with a seed produced by a rapeseed plant before transformation.

6. The rapeseed plant according to claim 2, wherein the antisense gene comprises a transcription initiation region operably joined to a napin coding sequence from the napA gene which is in an antisense orientation with respect to the transcription initiation sequence.

7. The rapeseed plant according to claim 1, wherein the antisense gene comprises a transcription initiation region operably joined to a cruciferin coding sequence from the cruA gene which is in an antisense orientation with respect to the transcription initiation sequence.

8. A seed produced by the rapeseed plant of claim 1, wherein the seed contains said antisense gene.

9. A seed produced by the rapeseed plant of claim 2, wherein the seed contains said antisense gene.

\* \* \* \* \*

UNITED STATES PATENT AND TRADEMARK OFFICE
CERTIFICATE OF CORRECTION

PATENT NO. :
DATED      :  5,530,192
INVENTOR(S) : June 25, 1996
              Junko MURASE et al.

It is certified that error appears in the above-indentified patent and that said Letters Patent is hereby corrected as shown below:

On the cover page, in item [73] Assignee: Please change "Mitsubishi Kasei Corporation" to --Mitsubishi Chemical Corporation--.

Signed and Sealed this

Twenty-fifth Day of February, 1997

Attest:

BRUCE LEHMAN

*Attesting Officer*      *Commissioner of Patents and Trademarks*

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 19 bases
        ( B ) TYPE: nucleic acid
        ( C ) STRANDEDNESS: single
        ( D ) TOPOLOGY: linear     ( i i ) MOLECULE TYPE: synthetic DNA     ( x i ) SEQUENCE DESCRIPTION: SEQ ID NO:1:

AAGCTTTCTT CATCGGTGA    19

( 2 ) INFORMATION FOR SEQ ID NO:2:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear     ( i i ) MOLECULE TYPE: synthetic DNA     ( x i ) SEQUENCE DESCRIPTION: SEQ ID NO:2:

CAAGATTAAA AACATACACG A    21

( 2 ) INFORMATION FOR SEQ ID NO:3:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear     ( i i ) MOLECULE TYPE: synthetic DNA     ( x i ) SEQUENCE DESCRIPTION: SEQ ID NO:3:

CTCATCAATA CAAACAAGAT    20

( 2 ) INFORMATION FOR SEQ ID NO:4:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear     ( i i ) MOLECULE TYPE: synthetic DNA     ( x i ) SEQUENCE DESCRIPTION: SEQ ID NO:4:

TATGTAAGGT TTTATCTAGG    20

( 2 ) INFORMATION FOR SEQ ID NO:5:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear     ( i i ) MOLECULE TYPE: synthetic DNA     ( x i ) SEQUENCE DESCRIPTION: SEQ ID NO:5:

```
        GCATGACGTT  ATTTATG                                                    17
```

( 2 ) INFORMATION FOR SEQ ID NO:6:

( i ) SEQUENCE CHARACTERISTICS:
    ( A ) LENGTH: 21 bases
    ( B ) TYPE: nucleic acid
    ( C ) STRANDEDNESS: single
    ( D ) TOPOLOGY: linear   ( i i ) MOLECULE TYPE: synthetic DNA   ( x i ) SEQUENCE DESCRIPTION: SEQ ID NO:6:

```
        AAAAACCACA  ACAACTAAGT  A                                              21
```

( 2 ) INFORMATION FOR SEQ ID NO:7:

( i ) SEQUENCE CHARACTERISTICS:
    ( A ) LENGTH: 18 bases
    ( B ) TYPE: nucleic acid
    ( C ) STRANDEDNESS: single
    ( D ) TOPOLOGY: linear   ( i i ) MOLECULE TYPE: synthetic DNA   ( x i ) SEQUENCE DESCRIPTION: SEQ ID NO:7:

```
        CACTGATGAG  TCCTGGAA                                                   18
```